United States Patent [19]  [11] 4,139,705
Dunbar et al.  [45] Feb. 13, 1979

[54] PYRAZOLOPYRIMIDINES

[75] Inventors: Joseph E. Dunbar; Louis E. Begin, both of Midland, Mich.

[73] Assignee: The Dow Chemical Company, Midland, Mich.

[21] Appl. No.: 799,018

[22] Filed: May 20, 1977

[51] Int. Cl.$^2$ ................ C07D 239/70; A61K 31/505
[52] U.S. Cl. .................................... 544/280; 544/116; 424/251
[58] Field of Search .................. 260/256.5 R; 544/280

[56] References Cited

U.S. PATENT DOCUMENTS 3,169,965  2/1965  Schmidt et al. .................... 260/256.5
3,600,389  8/1971  Druey et al. .................... 260/256.4 F Primary Examiner—Jose Tovar
Assistant Examiner—Lisa Jones
Attorney, Agent, or Firm—James W. Ambrosius

[57] ABSTRACT

Novel aminoalkyl purine and pyrazolopyrimidine compounds useful in the inhibition of blood platelet aggregation in animals.

4 Claims, No Drawings

PYRAZOLOPYRIMIDINES

SUMMARY OF THE INVENTION

The present invention is directed to novel aminoalkylthio purines and pyrazolopyrimidines represented by the general formula

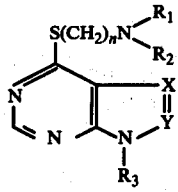

wherein $n$ represents an integer of from 1 to 3; $R_1$ and $R_2$ represent a lower alkyl group of from 1 to about 4 carbon atoms or taken together with the adjacent nitrogen represent the 6-membered heterocyclic ring morpholino; $R_3$ represents hydrogen, a lower alkyl having 1 or 2 carbon atoms, phenyl, or substituted phenyl having one or two halo substituents selected from the group consisting of chloro and bromo; and X and Y represent a carbon atom with its respective hydrogen or represent nitrogen with the proviso that when X is carbon, Y is nitrogen and when X is nitrogen, Y is carbon.

The present invention further includes the pharmaceutically-acceptable salts of the novel compounds described herein. Pharmaceutically-acceptable salts of the purine and pyrazolopyrimidine compounds refer to operable addition salts of the above compounds having anionic moieties which are relatively innocuous to animals at dosages consistent with good pharmacological activity so that the beneficial effects are not vitiated by the side effects ascribable to the anions. Representative salts include acid addition salts formed by the addition of inorganic acids such as hydrochloric, hydrobromic, and sulfuric acid or of organic acids such as lactic, maleic, succinic, fumaric, glutaric, citric, malic, methanesulfonic, p-toluenesulfonic, tartaric, and the like.

The compounds of the present invention have been shown to be effective as adenosine diphosphate induced platelet aggregation inhibitors when administered to an animal. Adenosine diphosphate, hereafter ADP, is a principal factor in the aggregation of blood platelets. Platelet aggregation in the blood stream of a mammal can lead to the formation of a thrombus. Agents which interfere with ADP induced platelet aggregation are of use as antithrombotic drugs.

In general, the compounds may be most conveniently prepared by coupling the purine or pyrazolopyrimidine moiety having a halo substitution with an aminoalkylthiol. The reaction may be summarized as follows:

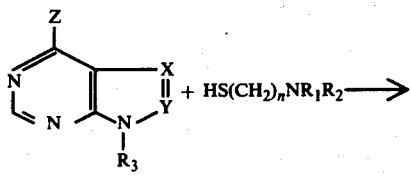

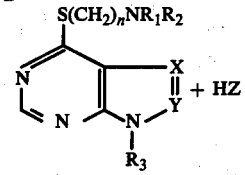

wherein Z represents a halogen and $R_1$, $R_2$, $R_3$, X, Y, and $n$ represent the same moieties as defined hereinbefore.

PREFERRED EMBODIMENTS OF THE INVENTION

The following examples will serve to illustrate the present invention but are not to be construed as limitations thereon.

EXAMPLE 1

Preparation of 4-((2-(4-Morpholinyl)ethyl)-thio)-1-phenyl-1H-pyrazolo (3,4-d)pyrimidine A mixture containing 5.0 grams (0.022 mole) of 4-chloro-1-phenyl-1H-pyrazolo(3,4-d)pyrimidine, 2.2 grams (0.022 mole) of triethylamine, 3.2 grams (0.022 mole) of 2-(morpholino)ethanethiol and 100 ml of ethanol was heated under reflux with stirring for about two hours. The reaction mixture was cooled, and the crystallized 4-((2-(4-morpholinyl)ethyl)thio)-1-phenyl-1H-pyrazolo(3,4-d) pyrimidine was filtered off and dried. The product was recrystallized from propanol-2 to give a white, crystalline solid having a melting point of 114°–115° C.

Elemental analysis showed carbon 59.8%, hydrogen 5.60% and nitrogen 20.48% compared to calculated values of carbon 59.8%, hydrogen, 5.61% and nitrogen 20.51%.

EXAMPLE 2

Preparation of 1-(4-Chlorophenyl)-4-((2-(diisopropylamino)ethyl)thio)-1H-pyrazolo(3,4-d)pyrimidine A mixture containing 5.0 grams (0.019 mole) of 4-chloro-1-(4-chlorophenyl)-1H-pyrazolo(3,4-d)pyrimidine, 3.7 grams (0.019 mole) of 2-(diisopropylamino)ethanethiol hydrochloride, 3.8 grams (0.040 mole) of triethylamine and 100 ml of ethanol was heated under reflux for two hours. The mixture was cooled and the title compound crystallized out and was collected on a filter, washed with water, and dried. The melting point was found to be 101°–102° C.

Elemental analysis showed carbon 58.38%, hydrogen 6.19%, and nitrogen 17.89% compared to calculated values of carbon 58.52%, hydrogen 6.20%, and nitrogen 17.96%.

Other compounds falling within the scope of the invention were also prepared using essentially the same method as already described. These compounds are:

1-(4-Chlorophenyl)-4-((2-(4-morpholinyl)-ethyl)thio)-1H-pyrazolo(3,4-d)pyrimidine, melting point 119°–119.5° C.

1-(4-Chlorophenyl)-4-((2-diethylamino)ethyl)thio)-1H-pyrazolo(3,4-d)pyrimidine Monohydrochloride, melting point 248°–249° C.

1-Methyl-4-((2-(4-morpholinyl)ethyl)thio)-1H-pyrazolo(3,4-d)pyrimidine Mono(4-methylbenzenesulfonate), melting point 187.5°–188° C.

6-((2-(Dimethylamino)ethyl)thio)-9H-purine Monohydrochloride, melting point 256.5°–257° C.

1-(3,4-Dichlorophenyl)-4-((2-diisopropylamino)ethyl)thio)pyrazolo(3,4-d)pyrimidine, melting point 109.5°–110° C.

EXAMPLE 3

Emboli formed in the vascular system of mice in response to the administration of ADP cause a stroke-like response that prevents mice from staying on an inclined screen. To illustrate the platelet aggregation inhibition effect of the compounds of the present invention, ten mice were dosed orally with 60 mg/kg of body weight of the compound 1-(4-chlorophenyl)-4-((2-(diethylamino)ethyl)thio)-1H-pyrazolo(3,4-d)pyrimidine monohydrochloride. One hour after compound administration, the mice were challenged with ADP (0.05 millimoles/kg) by injection via the tail vein and placed on an inclined screen. The unprotected control mice were unable to maintain their position on the screen. Six mice (60%) treated with platelet aggregation inhibitor were found to be protected from the ADP challenge and were able to remain on the screen.

The other compounds disclosed herein while displaying differing levels of activity as platelet aggregation inhibitors from the example above also showed significant activity as platelet aggregation inhibitors.

We claim:

1. A compound of the formula

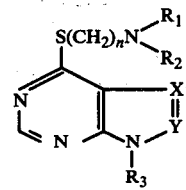

wherein $n$ represents an integer of from 1 to 3; $R_1$ and $R_2$ represent a lower alkyl group of from 1 to about 4 carbon atoms; $R_3$ represents phenyl, or substituted phenyl having one or two halo substituents selected from the group consisting of chloro and bromo; and X represents a carbon atom with its respective hydrogen and Y represents nitrogen and further including the pharmaceutically-acceptable salts thereof.

2. The compound of claim 1 which is 1-(4-chlorophenyl)-4-((2-(diisopropylamino)ethylthio)-1H-pyrazolo(3,4-d)pyrimidine and the pharmaceutically-acceptable salts thereof.

3. The compound of claim 1 which is 1-(4-chlorophenyl)-4-((2-diethylamino)ethylthio)-1H-pyrazolo(3,4-d)pyrimidine and the pharmaceutically-acceptable salts thereof.

4. The compound of claim 1 which is 1-(3,4-dichlorophenyl)-4-(2-(diisopropylamino)ethylthio)pyrazolo(3,4-d)pyrimidine and the pharmaceutically-acceptable salts thereof.

* * * * *